(12) United States Patent
Fitt, Sr. et al.

(10) Patent No.: US 6,211,384 B1
(45) Date of Patent: Apr. 3, 2001

(54) METHODS FOR THE ACYLATION OF AMINE COMPOUNDS

(75) Inventors: John Joseph Fitt, Sr., Denville; Prasad Koteswara Kapa, Parsippany, both of NJ (US)

(73) Assignee: Novartis Pharmaceuticals Corp., East Hanover, NJ (US)

( * ) Notice: Subject to any disclaimer, the term of this patent is extended or adjusted under 35 U.S.C. 154(b) by 0 days.

(21) Appl. No.: 09/385,722

(22) Filed: Aug. 30, 1999

(51) Int. Cl.$^7$ ............... C07D 207/04; C07C 231/02
(52) U.S. Cl. ............... 548/537; 548/538; 560/42; 564/142
(58) Field of Search ............... 564/142; 548/537, 548/538; 560/42

(56) References Cited

U.S. PATENT DOCUMENTS 5,625,058   4/1997   Pessa et al. ............... 540/226

FOREIGN PATENT DOCUMENTS

97/15579   5/1997   (WO) .
98/19998   5/1998   (WO) .

OTHER PUBLICATIONS

Fitt et al., "Sodium 2–Ethylhexanoate: A Mild Acid Scavenger Useful in Acylation of Amines," Tetrahedron Letters 39, (1998), p. 6991–6992.
Bose et al., "A Pratical Method for the Preparation of Nitriles from Primary Amides Under Non–Acidic Conditions," Synthesis 1999, No. 1, p. 64–65.
Highlights from the Literature: "Some Items of Interest of Process R&D Chemists and Engineers, Selected by the Editor," Organic Process Research & Development, vol. 2, No. 6, (1998), p. 340–343.
Jerry March, *Advanced Organic Chemistry: Reactions, Mechanisms, and Structure,* John Wiley & Sons, (1992), p. 430.

*Primary Examiner*—Shailendra Kumar
(74) *Attorney, Agent, or Firm*—John D. Thallemer

(57) ABSTRACT

Method for the acylation of amines are disclosed in which includes reacting a first reactant containing an amine group with a second reactant containing an acyl halide group, wherein the reaction takes place in the presence of secondary carboxylic acid salt form, of formula I:

$$R^4R^5CHCOOH \qquad I$$

wherein
  $R^4$ is an alkyl group having 1 to 10 carbon atoms; and
  $R^5$ is an alkyl group having 1 to 10 carbon atoms.

14 Claims, No Drawings

METHODS FOR THE ACYLATION OF AMINE COMPOUNDS

FIELD OF THE INVENTION

The present invention relates to the acylation of amine compounds. More particularly, the invention relates to forming acylated amines by reacting amine compounds and acyl halide compounds in the presence of a base or scavenger compound that has advantageous properties.

BACKGROUND OF INVENTION

When reacting acid chlorides with amines by known methods, those skilled in the art may be faced with certain concerns. It is generally desirable to conduct the acylation reaction using simple, practicable, high yielding, and environmentally friendly methods. In instances where the acylated amine product may be used as an intermediate in forming other compounds, additional criteria for the acylation reaction may arise. For example, classical Schotten-Baumann acylation conditions are impracticable for the acylation of prolinamide because both the starting material and the products are highly water-soluble and sparingly soluble in organic solvents. Although epoxypropane may possibly be used as an HCl scavenger in acylation reactions, epoxypropane has a low boiling point and may be considered environmentally unacceptable. Epoxypropane may also present an unacceptable carcinogenic risk. Finally, acylation with epoxypropane as the scavenger presents separate problems as the reaction in tetrahydrofuran is heterogeneous.

SUMMARY OF THE INVENTION

It is therefore an object of the present invention to provide a method for reacting amines with acyl halides.

Another object of the present invention is to provide a method for reacting amines with acyl halides in a simple, practicable, high yielding and environmentally friendly manner.

Another object of the present invention is to provide an economical method to produce acylated amines that may be used as intermediates in the synthesis of additional compounds.

To achieve these and other objects of the present invention, a method for the acylation of an amine is disclosed in which the process includes reacting a first reactant containing an amine group with a second reactant containing an acyl halide group, wherein the reaction takes place in the presence of secondary carboxylic acid of formula I:

$$R^4R^5CHCOOH \qquad \qquad I$$

wherein
  $R^4$ is an alkyl group having 1 to 10 carbon atoms; and
  $R^5$ is an alkyl group having 1 to 10 carbon atoms.

DETAILED DESCRIPTION OF INVENTION

In one aspect of the invention, the inventors have developed a simple, mild, and efficient method for the acylation of amines utilizing a secondary carboxylic acid salt of the formula I:

$$R^4R^5CHCOOH \qquad \qquad I$$

wherein
  $R^4$ is an alkyl group having 1 to 10 carbon atoms; and $R^5$ is an alkyl group having 1 to 10 carbon atoms.

Preferably, $R^4$ is an alkyl group having 1 to 5 carbon atoms, more preferably 1 to 3 carbon atoms. Preferably, $R^5$ is an alkyl group having 2 to 8 carbon atoms, more preferably 3 to 7 carbon atoms, most preferably 4 to 6 carbon atoms.

In another preferred embodiment, at least one of the alkyl groups $R^4$ or $R^5$ has at least 4 carbon atoms.

In a most preferred embodiment, the secondary carboxylic acid salt of formula I is sodium 2-ethylhexanoate. Sodium 2-ethylhexanoate is a mild and inexpensive base that is readily soluble in organic solvents such as toluene, ethers, and tetrahydrofuran. Sodium 2-ethylhexanoate may be produced by known methods, such as the reaction of sodium hydride with ethylhexanoic acid, or it may be purchased from chemical suppliers such as Aceto Corporation, Lake Success, N.Y.

As used in the acylation, the secondary carboxylic acid is preferably in the alkaline salt form. The salt form may contain, for example, sodium, potassium, or lithium as the anion.

It is noted that it may also be beneficial to add a compound of formula I to the reaction medium as the free acid in an amount effective to solubilize the first reactant containing an amine group.

As mentioned, the first reactant contains an amine group. Preferred compounds for the first reactant include, for example, compounds of the formula II:

$$R^1R^2\text{—NH} \qquad \qquad II$$

wherein
  $R^1$ and $R^2$ are, independently of one another, hydrogen, methyl, saturated or unsaturated $C_2$–$C_{20}$ alkyl, cycloalkyl, heterocyclyl, unsubstituted or substituted phenyl, with the proviso that both $R^1$ and $R^2$ are not hydrogen or
  $C_1$–$C_{20}$ alkyl, $C_3$–$C_8$ cycloalkyl, $C_3$–$C_8$ heterocyclyl, $C_6$–$C_{10}$aryl, or $C_5$–$C_{10}$ heteroaryl, which may be unsubstituted or substituted by halogen, carbonyl, —OH, -ester, acetoxy, CN, acetamido or
  $R^1$ and $R^2$ together form a ring having 3–10 carbon atoms and the ring is unsubstituted or substituted by halogen, carbonyl, —OH, ester, acetyl, $NH_2(CH_2)_xCO$—, R'OCO—, or CN, wherein x is 0 to 5.

In another preferred embodiment, $R^1$ and $R^2$ together form a ring having 3–10 carbon atoms and the ring is unsubstituted, or substituted by —$CONH_2$ or ester group.

In another preferred embodiment, $R^1$ and $R^2$ together form a ring having four carbon atoms and the ring is substituted by —$CONH_2$. A still further preferred embodiment lies in the use of prolinamide as the first reactant, where the —$CONH_2$ group is attached to the ring at a carbon atom adjacent the nitrogen.

In other preferred embodiments, the amine compound used as the first reactant may be an anthranilate, amino acid ester.

As the second reactant containing an acyl halide may be used. The acyl halide containing second reactant may, in one preferred embodiment, be represented by formula III:

$$R^3COCl \qquad \qquad III$$

wherein $R^3$ is methyl; ethyl; or
  a saturated or unsaturated, branched or unbranched $C_3$–$C_{10}$ alkyl, $C_3$–$C_{10}$ cycloalkyl, aryl, or heteroaryl, which may be unsubstituted or substituted by halogen, carbonyl, —OH, ester, acetyl, —OCOR'; or CN, $CONH_2$.

In another preferred embodiment, $R^3$ is $C_1$–$C_{10}$ alkyl, $C_1$–$C_{10}$ alkyl monosubstituted with a halogen, branched or unbranched $C_3$–$C_{10}$ alkyl, or $C_6H_5(CH_2)_y$— in which y is 0–10.

In more preferred embodiments, the acyl chloride used as the second reactant may be chloroacetyl chloride, bromoacetyl bromide, benzolyl chloride, or any activated ester group.

The acylation reaction may be conducted in typical organic solvents, including tetrahydrofuran, t-butyl methyl ether, ethyl or isopropyl acetate, heptane etc. The acylation reaction may be run at a temperature ranging from about −30 to about 40 C., preferably about −20 to about 25 C.

Depending on the intended use of acylated amine product, sodium chloride formed during the reaction may be washed out with water or separated by extraction into organic solvents.

In the preferred embodiment in which prolinamide is acylated, the acylated prolinamide may be used as an intermediate in the production of the N-(substituted glycyl) 2-cyanopyrrolidines. Because it has recently been discovered that certain N-(substituted glycyl)-2-cyanopyrrolidines (hereinafter "the cyanopyrrolidine compounds") inhibit DPP-IV it has become desirable to produce N-(substituted glycyl)-2-cyanopyrrolidines as pharmaceutical products suitable for administration to mammals. Cyanopyrrolidine compounds that may be synthesized using the acylated prolinamide produced by our process are disclosed in WO 98/19998, the entire contents of which are incorporated herein by reference.

EXAMPLE 1

A 5 L, 4-necked, round-bottomed flask was flushed with nitrogen. The flask was charged under nitrogen with 171.2 g of L-prolinamide, 275 g of sodium 2-ethylhexanoate, and 1.36 kg of t-butyl methyl ether to form a reaction mixture. The mixture was stirred at an internal temperature of 20±5 C. and 227 g of 2-ethylhexanoic acid was added dropwise over 15 minutes. The reaction mixture was stirred until suspended solvents dissolved to form a clear solution, and was then cooled to −15±C. 178 g of chloroacetyl chloride was added dropwise and the reaction mixture was maintained at −15±5 C. for a 75 minute addition period. A precipitate formed by the end of the addition period, and the mixture was stirred at −15±5 C. for 1 hour. The mixture was warmed to 20±5 C., and then diluted with 0.76 kg of t-butyl methyl ether.

The mixture was filtered to form a filter cake, and the filter cake and flask were washed with 0.76 kg of t-butyl methyl ether. The filter cake was air-dried for 1 hour, transferred to a second 4-necked flask, and 1.3 kg of heptane was added. The resulting mixture was stirred at 20±5 C. for about 4 hours and filtered again. The resulting filter cake was washed again with 1.3 kg of heptane, dried at 20±5 C. for about 24 hours to give 373 g of the acylated prolinamide product, mixed with sodium chloride, as a white solid. The reaction scheme for the acylation of prolinamide is shown below:

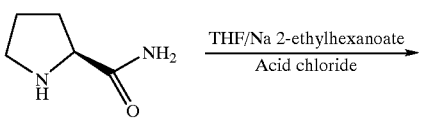

THF/Na 2-ethylhexanoate
Acid chloride

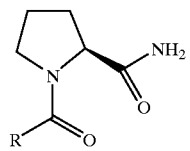

EXAMPLE 2

According to procedures substantially similar to that described in Example 1, prolinamide was acylated with various acid chlorides. The acid chlorides used and observed yields of acylated prolinamide are shown in the Table below:

| Acid Chloride | Yield % |
|---|---|
| CH$_3$COCl | 80 |
| t-BuCOCl | >90 |
| PhCH$_2$COCl | >90 |

EXAMPLE 3

By a method substantially similar to that described in Example 1, the acylation reaction shown below was successfully performed.

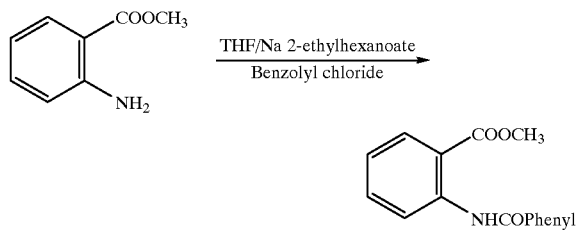

An 83% yield of the acylated product was observed.

EXAMPLE 4

By a method substantially similar to that described in Example 1, the acylation reaction shown below was successfully performed.

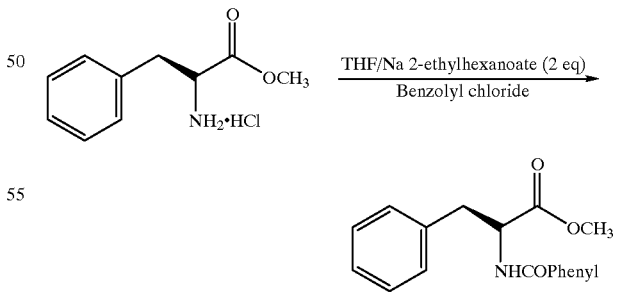

A 95% yield of the acylated product was observed.

Other embodiments of the present invention will be apparent to those skilled in the art from consideration of the specification and practice of the invention disclosed herein. It is intended that the specification be considered as exemplary only, with a true scope and spirit of the invention being indicated by the following claims.

We claim:

1. A method for the acylation of an amine in which the method comprises reacting a first reactant containing an amine group with a second reactant containing an acyl halide group, wherein the reaction takes place in the presence of a secondary carboxylic acid of formula I:

$$R^4R^5CHCOOH \qquad I$$

wherein $R^4$ is an alkyl group having 1 to 10 carbon atoms; and $R^5$ is an alkyl group having 1 to 10 carbon atoms.

2. The method of claim 1, wherein $R^4$ is an alkyl group having 1 to 3 carbon atoms; and $R^5$ is an alkyl group having 4 to 6 carbon atoms.

3. The method of claim 1, wherein the secondary carboxylic acid is 2-ethylhexanoic acid, in the salt form.

4. The method of claim 1, wherein the secondary carboxylic acid is in salt form.

5. The method of claim 1, wherein the first reactant and the secondary carboxylic acid are combined with each other prior to combination with the second reactant.

6. The method of claim 1, wherein the acyl halide group is an acyl chloride.

7. The method of claim 1, wherein the first reactant is an aminoacid amide, amino acid ester or an anthranilate.

8. The method of claim 1, wherein the first reactant is prolinamide.

9. The method of claim 1, wherein the first reactant is a compound of formula II:

$$(R^1R^2\text{---}NH) \qquad II$$

the second reactant is an acid chloride of formula III:

$$R^3COCl \qquad III$$

wherein $R^1$ and $R^2$ are, independently of one another, hydrogen, methyl, saturated or unsaturated $C_2$–$C_{20}$ alkyl, cycloalkyl, heterocyclyl, substituted or unsubstituted phenyl which in turn may be substituted by halogen, carbonyl, hydroxy, acetoxy, CN, ester or amide group. with the proviso that both $R^1$ and $R^2$ are not hydrogen; or $C_1$–$C_{20}$ alkyl, $C_3$–$C_8$ cycloalkyl, $C_3$–$C_8$ heterocyclyl, $C_6$–$C_{10}$ aryl, or $C_5$–$C_{10}$ heteroaryl, which may be unsubstituted or substituted by halogen, carbonyl, —OH, acetoxy, ester, CN, or amide, or $R^1$ and $R^2$ together form a ring having 3–8 carbon atoms and the ring is unsubstituted or substituted by halogen, carbonyl, —OH, estrer, acetyl, $NH_2(CH_2)_xCO$—, R'OCO—, CN or amide, wherein x is 0 to 5; and $R^3$ is methyl; ethyl; or a saturated or unsaturated, branched or unbranched $C_3$–$C_{10}$ alkyl, $C_3$–$C_{10}$ cycloalkyl, aryl, or heteroaryl, which may be unsubstituted or substituted by halogen, carbonyl, —OH, ester, acetyl, —OCOR'; or CN, $CONH_2$.

10. The method of claim 9, wherein $R^1$ is $R^6CO$— in which $R^6$ is selected from the group consisting of $C_1$–$C_{10}$ alkoxy; phenoxy; $C_3$–$C_8$ cycloalkyl, $C_3$–$C_{10}$ heterocyclyl, unsubstituted phenyl; phenyl substituted with $C_1$–$C_{10}$ alkyl, $C_1$–$C_{10}$ alkoxy, ester, or halogen; and $R^2$ is hydrogen.

11. The method of claim 9, wherein $R^1$ is $C_6$–$C_{10}$ aryl-$(CH_2)_x$—CH—COO—$(C_1$–$C_{10}$ alkyl) or $C_6$–$C_{10}$ aryl substituted by R'COO— and $R^2$ is hydrogen.

12. The method of claim 9, wherein $R^1$ and $R^2$ together form a ring having 3–10 carbon atoms and the ring is unsubstituted, or substituted by —$CONH_2$.

13. The method of claim 9, wherein $R^1$ and $R^2$ together form a ring having four carbon atoms and the ring is substituted by —$CONH_2$.

14. The method of claim 9, wherein $R^3$ is $C_1$–$C_{10}$ alkyl, $C_1$–$C_{10}$ alkyl monosubstituted with a halogen, branched or unbranched $C_3$–$C_8$ alkyl, or $C_6H_5(CH_2)_y$— in which y is 0–10.

* * * * *